United States Patent
Bai et al.

(10) Patent No.: US 11,396,547 B2
(45) Date of Patent: Jul. 26, 2022

(54) ANTI-EGFR AND ANTI-CD3 BISPECIFIC ANTIBODY AND USES THEREOF

(71) Applicants: BEIJING DONGFANG BIOTECH CO., LTD., Beijing (CN); BEIJING JINGYITAIXIANG TECHNOLOGY DEVELOPMENT CO. LTD., Beijing (CN)

(72) Inventors: Yi Bai, Beijing (CN); Wen Zhang, Beijing (CN); Meng Xu, Beijing (CN); Shuang Pei, Beijing (CN); Yanlu Zan, Beijing (CN); Shengmei Wen, Beijing (CN)

(73) Assignees: BEIJING DONGFANG BIOTECH CO., LTD., Beijing (CN); BEIJING JINGYITAIXIANG TECHNOLOGY DEVELOPMENT CO. LTD., Beijing (CN)

( * ) Notice: Subject to any disclaimer, the term of this patent is extended or adjusted under 35 U.S.C. 154(b) by 527 days.

(21) Appl. No.: 16/321,438

(22) PCT Filed: Sep. 28, 2017

(86) PCT No.: PCT/CN2017/103896
§ 371 (c)(1),
(2) Date: Jan. 28, 2019

(87) PCT Pub. No.: WO2018/068652
PCT Pub. Date: Apr. 19, 2018

(65) Prior Publication Data
US 2021/0277127 A1 Sep. 9, 2021

(30) Foreign Application Priority Data

Oct. 11, 2016 (CN) .......................... 201610886938.7

(51) Int. Cl.
*C07K 16/28* (2006.01)
(52) U.S. Cl.
CPC ...... *C07K 16/2863* (2013.01); *C07K 16/2809* (2013.01); *C07K 2317/14* (2013.01); *C07K 2317/31* (2013.01); *C07K 2317/56* (2013.01); *C07K 2317/622* (2013.01)
(58) Field of Classification Search
CPC ............ C07K 16/2863; C07K 16/2809; C07K 2317/14; C07K 2317/31; C07K 2317/56; C07K 2317/622; C07K 16/30; C07K 16/468; C07K 2317/52; C07K 2317/92; C07K 2317/94; A61K 2039/505; A61P 35/00
See application file for complete search history.

(56) References Cited

U.S. PATENT DOCUMENTS

| 7,919,089 B2 * | 4/2011 | Kufer ................ C07K 16/3076 424/136.1 |
| 9,611,325 B2 * | 4/2017 | Zhou ................ C07K 16/2887 |
| 10,919,977 B2 * | 2/2021 | Gao ................ A61K 39/39558 |
| 2009/0252731 A1 | 10/2009 | Hansen et al. |
| 2012/0189630 A1 | 7/2012 | Bigner et al. |
| 2015/0004421 A1 | 1/2015 | Fujiwara et al. |
| 2015/0044216 A1 * | 2/2015 | Wu ................ A61K 47/6879 424/136.1 |

FOREIGN PATENT DOCUMENTS

| CA | 2859767 A1 | 6/2013 |
| CN | 1133886 A | 10/1996 |
| CN | 1603345 A | 4/2005 |
| CN | 104203981 A | 12/2014 |
| CN | 104341504 A | 2/2015 |
| CN | 104774268 A | 7/2015 |
| CN | 106632681 A | 5/2017 |
| JP | H08280387 A | 10/1996 |
| WO | WO-2004106383 A1 * | 12/2004 ......... C07K 16/3076 |
| WO | 2005004809 A2 | 1/2005 |
| WO | 2012020622 A1 | 2/2012 |
| WO | 2014165818 A2 | 10/2014 |
| WO | 2015013671 A1 | 1/2015 |
| WO | 2015146437 A1 | 10/2015 |

(Continued)

OTHER PUBLICATIONS

Hiroki Hayashi et al: "A highly effective and stable bispecific diabody for cancer immunotherapy: cure of xenografted tumors by bispecific diabody and T-LAK cells". Cancer Immunol Immunother (2004) 53: 497-509, Nov. 25, 2003 (Nov. 25, 2003).
KR first examination report dated Apr. 29, 2020 re: Application No. 10-2019-7003194, pp. 1-8.
AU first Office Action dated Oct. 25, 2019 re: Application No. 2017343414, pp. 1-9, citing: US 2015/0044216 A1, WO 2015/013671 A1 and WO 2016/014974 A2.
Ryutaro Asano et al. "Functionalization of Bispecific Therapeutic Antibodies Based on Protein Engineering". Yakugaku Zasshi : Journal of the Pharmaceutical Society of Japan, Jan. 1, 2015, 135(7):851-856.

(Continued)

*Primary Examiner* — Phuong Huynh
(74) *Attorney, Agent, or Firm* — Gang Yu

(57) ABSTRACT

An anti-Epidermal Growth Factor Receptor (EGFR) and anti-Cluster-of-Differentiation (CD3) bispecific antibody and uses thereof are provided. The bispecific antibody can specifically bind to antigen epidermal growth factor receptor (EGFR) on tumor cell surface and antigen CD3 molecule on immune cell surface. The single-chain antibody (ScFv) of an anti-CD3 antibody is located at the C terminal of the constant region of the anti-EGFR antibody. Further provided are a preparation method of the bispecific antibody and clinical applications of the bispecific antibody. The bispecific antibody has high affinity, and is used for treating tumor diseases caused by high expression or abnormal expression of the EGFR and other diseases caused by other overexpression of the EGFR.

9 Claims, 8 Drawing Sheets

Specification includes a Sequence Listing.

(56) References Cited

FOREIGN PATENT DOCUMENTS

| WO | 2015146438 | A1 | 10/2015 |
| WO | 2016014974 | A2 | 1/2016 |
| WO | 2016071004 | A1 | 5/2016 |
| WO | 2016115274 | A1 | 7/2016 |

OTHER PUBLICATIONS

JP first Office Action dated Jan. 14, 2020 re: Application No. 2019-505507, pp. 1-4.
Reusch, U. et al. Anti-CD3 X Anti-Epidermal Growth Factor Receptor (EGFR) Bispecific Antibody Redirects T-Cell Cytolytic Activity to EGFR-Positive Cancers In vitro and in an Animal Model. Clin. Cancer Res. Jan. 1, 2006 (Jan. 1, 2006), 12(1), pp. 183-190.
Asano, R. et al. Highly Enhanced Cytotoxicity of a Dimeric Bispecific Diabody, the hEx3 Tetrabody. The Journal of Biological Chemistry. Jul. 2, 2010 (Jul. 2, 2010), 285(27), pp. 20844-20849.
JP second Office Action dated Sep. 23, 2020 re: Application No. 2019-505507, pp. 1-3.
Spiess Christoph et al: "Alternative molecular formats and therapeutic applications for bispecific antibodies". Molecular Immunology, Pergamon, GB,vol. 67, No. 2, , Jan. 27, 2015(Jan. 27, 2015), pp. 95-106.
EP first search report dated Apr. 28, 2020 re: Application No. 17860812.1, pp. 1-8.

\* cited by examiner

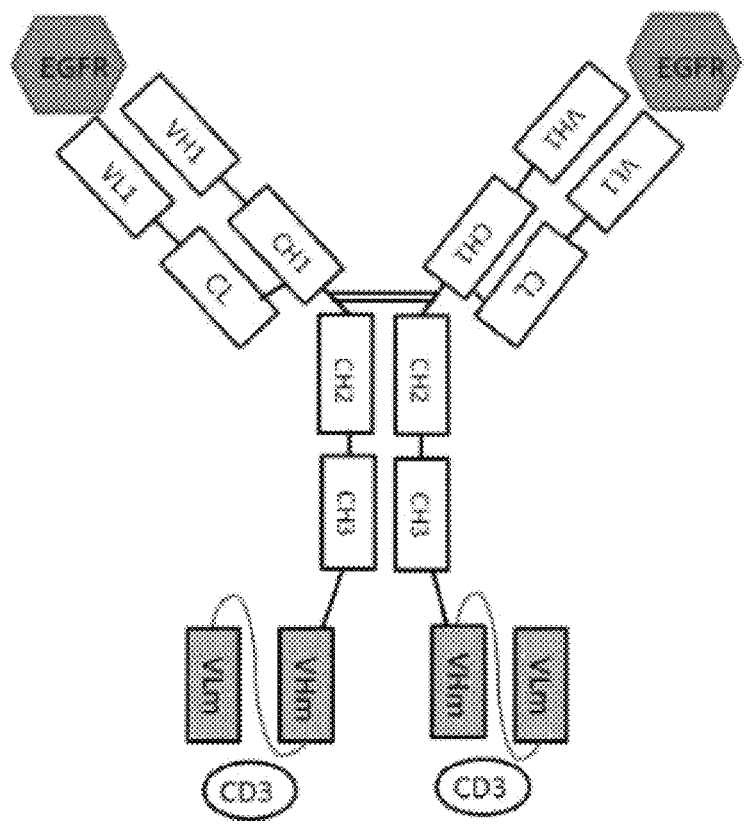
Fig. 1
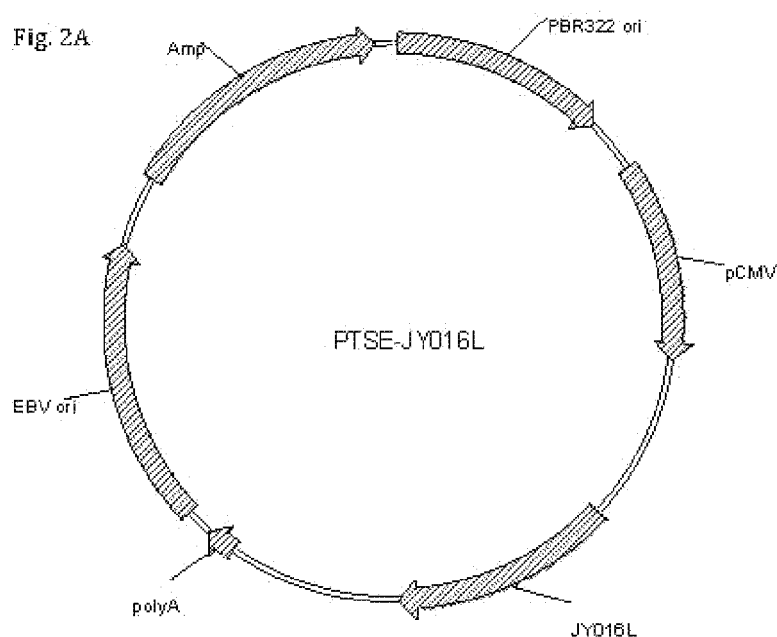

Fig. 4A
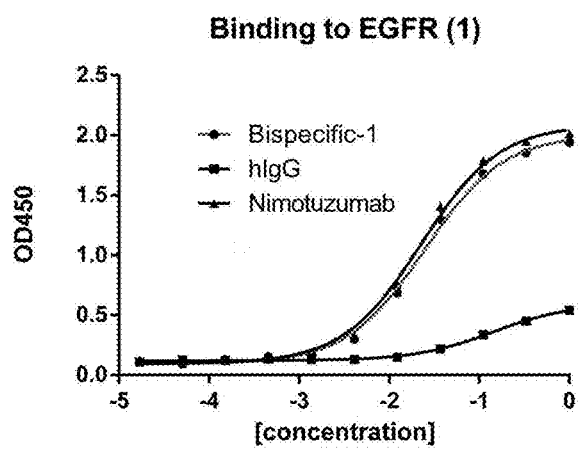
Fig. 4B
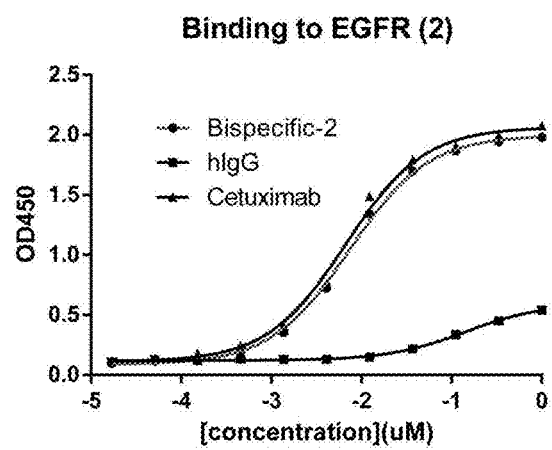
Fig. 4C
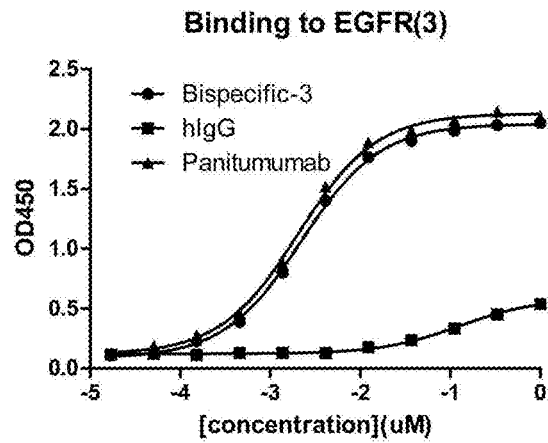
Fig. 4D
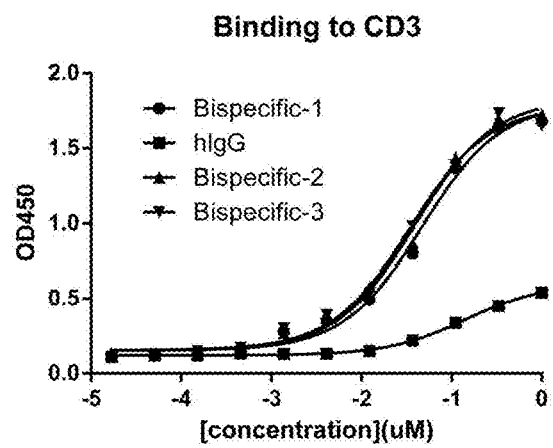
Fig. 4

Fig. 5A
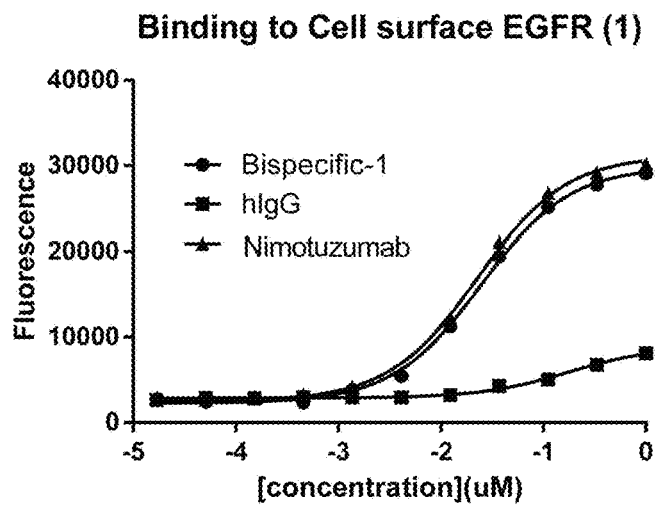
Fig. 5B
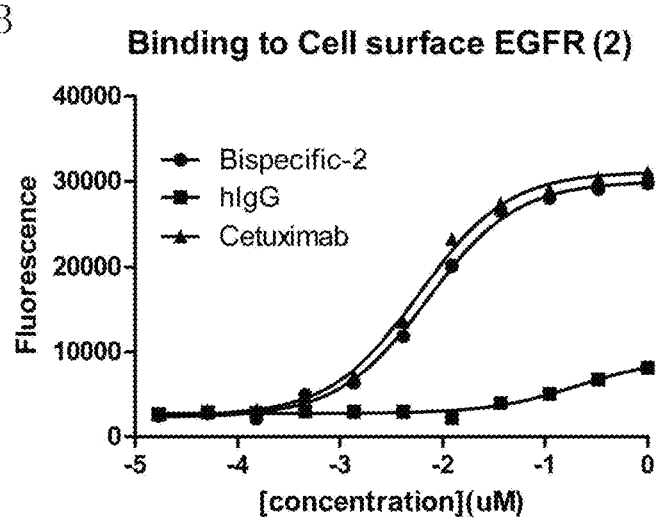
Fig. 5C
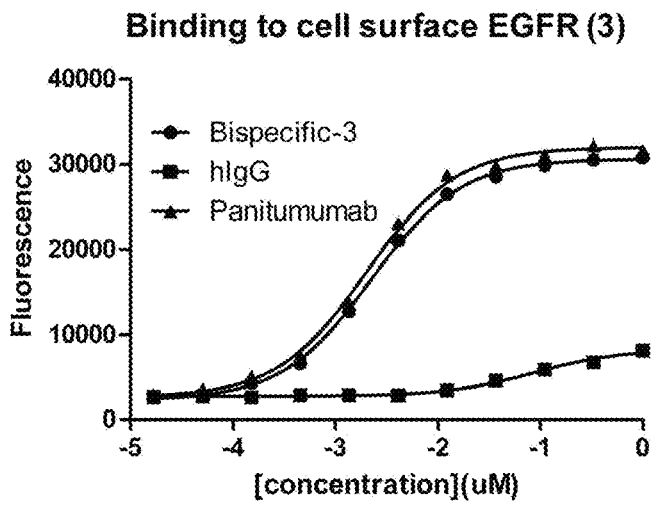
Fig. 5

SEQUENCE LISTING

<160> NUMBER OF SEQ ID NOS: 13

<210> SEQ ID NO 1
<211> LENGTH: 123
<212> TYPE: PRT
<213> ORGANISM: unknown
<220> FEATURE:
<223> OTHER INFORMATION: heavy chain variable region of nimotuzumab

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
                20                  25                  30

Tyr Ile Tyr Trp Val Lys Gln Arg Pro Gly Gln Gly Leu Glu Trp Ile
            35                  40                  45

Gly Gly Ile Asn Pro Thr Ser Gly Gly Ser Asn Phe Asn Glu Lys Phe
        50                  55                  60

Lys Thr Lys Ala Thr Leu Thr Val Asp Glu Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Leu Thr Val Ser Ser
        115                 120

<210> SEQ ID NO 2
<211> LENGTH: 119
<212> TYPE: PRT
<213> ORGANISM: unknown
<220> FEATURE:
<223> OTHER INFORMATION: heavy chain variable region of cetuximab

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 3
<211> LENGTH: 119
<212> TYPE: PRT
<213> ORGANISM: unknown
<220> FEATURE:
<223> OTHER INFORMATION: heavy chain variable region of panitumumab

<400> SEQUENCE: 3

-continued

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65              70                  75                  80

Ser Leu Lys Leu Ser Ser Val Thr Ala Ala Asp Thr Ala Ile Tyr Tyr
            85                  90                  95

Cys Val Arg Asp Arg Val Thr Gly Ala Phe Asp Ile Trp Gly Gln Gly
        100                 105                 110

Thr Met Val Thr Val Ser Ser
        115

<210> SEQ ID NO 4
<211> LENGTH: 112
<212> TYPE: PRT
<213> ORGANISM: unknown
<220> FEATURE:
<223> OTHER INFORMATION: light chain variable region of nimotuzumab

<400> SEQUENCE: 4

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Asp Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Arg Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Tyr
            85                  90                  95

Ser His Val Pro Trp Thr Phe Gly Gly Gly Thr Lys Leu Glu Ile Lys
        100                 105                 110

<210> SEQ ID NO 5
<211> LENGTH: 107
<212> TYPE: PRT
<213> ORGANISM: unknown
<220> FEATURE:
<223> OTHER INFORMATION: light chain variable region of cetuximab

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser

```
                65                  70                  75                  80
Glu Asp Ile Ala Asp Tyr Tyr Cys Gln Gln Asn Asn Asn Trp Pro Thr
                    85                  90                  95

Thr Phe Gly Ala Gly Thr Lys Leu Glu Leu Lys
            100                 105

<210> SEQ ID NO 6
<211> LENGTH: 107
<212> TYPE: PRT
<213> ORGANISM: unknown
<220> FEATURE:
<223> OTHER INFORMATION: light chain variable region of panitumumab

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 7
<211> LENGTH: 240
<212> TYPE: PRT
<213> ORGANISM: unknown
<220> FEATURE:
<223> OTHER INFORMATION: anti-CD3 single-chain antibody

<400> SEQUENCE: 7

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160
```

```
Ser Ser Val Ser Tyr Met Asn Trp Tyr Gln Gln Lys Ser Gly Thr Ser
            165                 170                 175

Pro Lys Arg Trp Ile Tyr Asp Thr Ser Lys Val Ala Ser Gly Val Pro
        180                 185                 190

Tyr Arg Phe Ser Gly Ser Gly Ser Gly Thr Ser Tyr Ser Leu Thr Ile
            195                 200                 205

Ser Ser Met Glu Ala Glu Asp Ala Ala Thr Tyr Tyr Cys Gln Gln Trp
        210                 215                 220

Ser Ser Asn Pro Leu Thr Phe Gly Ala Gly Thr Lys Leu Glu Leu Lys
225                 230                 235                 240

<210> SEQ ID NO 8
<211> LENGTH: 119
<212> TYPE: PRT
<213> ORGANISM: unknown
<220> FEATURE:
<223> OTHER INFORMATION: heavy chain variable region of an anti-CD3
      single-chain antibody

<400> SEQUENCE: 8

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
        100                 105                 110

Thr Thr Leu Thr Val Ser Ser
        115

<210> SEQ ID NO 9
<211> LENGTH: 106
<212> TYPE: PRT
<213> ORGANISM: unknown
<220> FEATURE:
<223> OTHER INFORMATION: light chain variable region of the anti-CD3
      single-chain antibody

<400> SEQUENCE: 9

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
            85                  90                  95
```

```
Phe Gly Ala Gly Thr Lys Leu Glu Leu Lys
            100                 105

<210> SEQ ID NO 10
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: PEPTIDE
<222> LOCATION: (5)..(5)
<223> OTHER INFORMATION: Xaa is Ala or Ser

<400> SEQUENCE: 10

Gly Gly Gly Gly Xaa
1               5

<210> SEQ ID NO 11
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: PEPTIDE
<222> LOCATION: (5)..(5)
<223> OTHER INFORMATION: Xaa is Ala or Ser
<220> FEATURE:
<221> NAME/KEY: PEPTIDE
<222> LOCATION: (10)..(10)
<223> OTHER INFORMATION: Xaa is Ala or Ser

<400> SEQUENCE: 11

Gly Gly Gly Gly Xaa Gly Gly Gly Gly Xaa
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthesized
<220> FEATURE:
<221> NAME/KEY: PEPTIDE
<222> LOCATION: (5)..(5)
<223> OTHER INFORMATION: Xaa is Ala or Ser
<220> FEATURE:
<221> NAME/KEY: PEPTIDE
<222> LOCATION: (10)..(10)
<223> OTHER INFORMATION: Xaa is Ala or Ser
<220> FEATURE:
<221> NAME/KEY: PEPTIDE
<222> LOCATION: (15)..(15)
<223> OTHER INFORMATION: Xaa is Ala or Ser

<400> SEQUENCE: 12

Gly Gly Gly Gly Xaa Gly Gly Gly Gly Xaa Gly Gly Gly Gly Xaa
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: Synthesized
<220> FEATURE:
<221> NAME/KEY: PEPTIDE
<222> LOCATION: (5)..(5)
<223> OTHER INFORMATION: Xaa is Ala or Ser
<220> FEATURE:
<221> NAME/KEY: PEPTIDE
```

```
<222> LOCATION: (10)..(10)
<223> OTHER INFORMATION: Xaa is Ala or Ser
<220> FEATURE:
<221> NAME/KEY: PEPTIDE
<222> LOCATION: (15)..(15)
<223> OTHER INFORMATION: Xaa is Ala or Ser
<220> FEATURE:
<221> NAME/KEY: PEPTIDE
<222> LOCATION: (20)..(20)
<223> OTHER INFORMATION: Xaa is Ala or Ser

<400> SEQUENCE: 13

Gly Gly Gly Gly Xaa Gly Gly Gly Gly Xaa Gly Gly Gly Gly Xaa Gly
1               5                   10                  15

Gly Gly Gly Xaa
            20
```

US 11,396,547 B2

ANTI-EGFR AND ANTI-CD3 BISPECIFIC ANTIBODY AND USES THEREOF

TECHNICAL FIELD

The invention relates to the field of biotechnology, and particularly to a method for constructing and preparing a bispecific antibody against Epidermal Growth Factor Receptor (EGFR) and Cluster-of-Differentiation 3 (CD3), and uses of the antibody in diseases.

BACKGROUND

The Bispecific Antibody (BiAb) is an artificial antibody composed of two different antibody fragments, and is capable of specifically recognizing and binding two different antigens or two different epitopes.

Monoclonal antibodies are widely applied to treat cancer, inflammation and other diseases. Since these antibodies all have single target, many patients may not fully respond to monotherapy and often have resistance to drugs. The bispecific antibody is capable of simultaneously recognizing two different antigens or epitopes and can serve as a medium to redirect Immunological effector cells, such as natural killer cells and T cells, and enhances an effect of killing tumor cells. In addition, the bispecific antibody may be further located at two different antigens of the same cell to change cell signals including a cancer spread signal or an inflammatory signal. With long-term research and development, multiple forms of bispecific antibodies appear, such as a bispecific microantibody, a double-chain antibody, a single-chain bivalent antibody, a polyvalent bispecific antibody and the like. These bispecific antibodies are basically divided into two major categories: Fc-containing antibodies and Fc-free antibodies. The former has excellent solubility, stability and half life, while an Fc Antibody Dependent Cell mediated Cytotoxicity (ADCC) and Complement-Dependent Cytotoxcity (CDC) may bring some additive effects needed by treatment. By contrast, the Fc-deficient bispecific antibody is completely dependent on antigen binding capacity to achieve therapeutic effect. In addition, the Fc protein may prolong half life of a drug protein (or a peptide) in vivo, thereby prolonging action time of an active molecule in vivo.

The tumor cell surface antigen Epidermal Growth Factor Receptor (EGFR): the epidermal growth factor receptor is widely distributed on the membrane of epithelial cells except for vascular tissues. As a molecular weight of about 180KDa transmembrane protein, EGFR has a ligand-induced tyrosine protein kinase activity and is a member of the conserved receptor family ErbB. Other members of the family include HER2/Neu/ErbB2, HER3/ErbB3 and HER4/ErbB4. Common characteristics of ErbB receptors are as follows: each ErbB receptor includes an Extracellular (EC) ligand binding domain, a single transmembrane domain composed of two repetitive cysteine rich regions, and an intracellular sequence including tyrosine protein kinase and autophosphorylation sites; after binding of ligands and receptors, dimerization of receptors is caused, and homodimers or heterodimers are formed; the dimerized receptors are subjected to crosslinked phosphorylation to activate a TK subregion in an intracellular region so as to excite next-level signal transduction, thereby causing cell proliferation and transformation. The EGFR is related to tumor cell proliferation, angiogenesis, tumor invasion, metastasis and cell apoptosis inhibition, and the mechanisms include: enhancement of downstream signal transduction caused by high expression of the EGFR, continuous activation of EGFR caused by increase of a mutant EGFR receptor or ligand expression, action enhancement of an autocrine loop, destruction of a receptor down-regulation mechanism, activation of an abnormal signal transduction pathway, and the like. Research shows that the EGFR has high expression or abnormal expression in many solid tumors, and is related to tumor cell proliferation, angiogenesis, tumor invasion, metastasis and cell apoptosis inhibition. Over-expression of the EGFR plays a significant role in tumor progression, and the over-expression of the EGFR exists in tissues of spongiocytoma, lung cancer, prostatic cancer, pancreatic cancer and the like.

The immune cell surface antigen Cluster-of-Differentiation 3 (CD3): CD3 molecule is an important differentiation antigen on a T cell membrane, is a characteristic sign of mature T cells, and is composed of 6 peptide chains. The TCR-CD3 complex, is composed of CD3 T Cell Receptor (TCR) with non-covalent bonds. The CD3 molecule participates in intracytoplasmic assembly of the TCR-CD3 complex, and transmits an antigen stimulating signal by Immunoreceptor Tyrosine-based Activation Motif (ITAM) of each polypeptide chain cytoplasmic domain. The main effects of CD3 molecule include stabilizing a TCR structure and transmitting a T cell activation signal. After the TCR specifically recognizes and binds with antigens, the CD3 participates in signal transduction into T cell cytoplasm. As a first signal inducing T cell activation, CD3 plays important roles in T cell antigen recognition and immune response generation processes.

In medicine, particularly in tumor immunotherapy, the bispecific antibody has excellent effects and prospects, is capable of simultaneously binding the parts of tumor cells and specific antigen-antiimmune active cells CD16 or CD3 on immune cells, and has an effect of activating NK cells or T cell. The antitumor specific antigen part can specially bind to the tumor cells, the immune cells are targeted to the tumor cells, and the concentration of local NK cells or T cells is increased, thereby enabling the Immunological effector cells to achieve a specific killing effect on the tumor cells. In the prior art, the EGFR and CD3 bispecific antibody drug product successfully marketed does not exist, and the technology is to be studied.

Relative to the Chinese patent CN201510030519.9, the present invention adopts a tetravalent bispecific antibody, and biological activity of the anti-EGFR antibody is completely remained; the tetravalent bispecific antibody is capable of well recognizing tumor antigen and effect cells (T cells, NK cells and the like), thereby well achieving biological activity of the bispecific antibody. The U.S. Pat. No. 9,249,217 B2 adopts a form of single-chain antibody ScFv-ScFv (BITE), and BITE is bivalent and does not have any Fc fragment. Compared with the BITE, in addition to advantages of the tetravalent antibody, the invention further contains Fc fragments; and the Fc fragments are capable of prolonging half life of effector molecules in vivo, thereby prolonging the action time of the effector molecules in vivo.

SUMMARY

The invention provides a bispecific antibody. The bispecific antibody adds an anti-Cluster-of-Differentiation 3 (CD3) ScFv sequence at C-terminal of an anti-EGFR antibody. The bispecific antibody retains a complete molecular structure of the anti-EGFR antibody and increases the capacity of binding to the CD3 antigen, since maintaining the biological activity of the original EGFR antibody in vivo, meanwhile targeting immunological effector cells to tumor cells by specifically recognizing two different antigens, thereby increasing the effect of immunological effector cells on killing tumor cells.

The invention provides an anti-EGFR and anti-CD3 specific antibody and the use thereof.

The bispecific antibody includes (a) a complete monoclonal antibody, (b) a single-chain antibody ScFv and (c) a linker, the (a) specifically binds to an EGFR antigen and consists of two antibody heavy chains and two antibody light chains; the (b) specifically binds to an immune cell antigen CD3, and the (b) refers to two single-chain antibodies ScFv; the two single-chain antibodies ScFv of the (b) are respectively linked with C terminals of the two antibody heavy chains of the (a) by the (c) linker.

Herein, the (c) linker in the bispecific antibody has an amino acid sequence of $(GGGGX)_n$, X includes Ser or Ala, preferably Ser; and n is a natural number of 1-4, preferably 3.

Herein, the (a) complete monoclonal antibody in the bispecific antibody consists of two light chains and two heavy chains, each heavy chain and each light chain are connected by disulfide bonds, and the two heavy chains are connected by disulfide bonds in a hinge region. Variable regions of the heavy chains and the light chains specifically bind to EGFR antigen of tumor cells.

Herein, a heavy chain constant region of the (a) complete monoclonal antibody is one of IgG1 IgG2, IgG3 or IgG4, preferably IgG2.

Herein, an amino acid sequence of a heavy chain variable region of the (a) complete monoclonal antibody is one of SEQ ID NO 1, SEQ ID NO 2 or SEQ ID NO 3; and an amino acid sequence of a light chain variable region of the (a) complete monoclonal antibody is one of SEQ ID NO 4, SEQ. ID NO 5 or SEQ ID NO 6. An amino acid sequence of a heavy chain variable region of the (b) single-chain antibody ScFv is SEQ ID NO 8, and an amino acid sequence of a light chain variable region of the (b) single-chain antibody ScFv is SEQ ID NO 9.

Herein, amino acid sequences of the two single-chain antibodies ScFv of the (b) are both SEQ ID NO 7.

Herein, each of the single-chain antibodies ScFv of the (b) consists of a heavy chain variable region, a (c) linker and a light chain variable region, the heavy chain variable region and the light chain variable region specifically bind to the CD3 antigen on immune cell surface; and the (c) linker has an amino acid sequence of $(GGGGS)_n$, herein n is a natural number of 1-4, preferably $(GGGGS)_3$.

Herein, an expression vector of the bispecific antibody is constructed, herein the bispecific antibody may be constructed into a vector, or respectively constructed into two different vectors.

Herein, the constructed vector is transfected into a host cell by genetic engineering method, and the host cell include a prokaryotic cell, a yeast cell or a mammalian cell such as CHO cell, NS0 cell or other mammalian cells, preferably the CHO cell.

Herein, the bispecific antibody is obtained by a conventional immunoglobulin method, including protein A affinity chromatography and ion exchange, hydrophobic chromatography or a molecular sieve process.

Herein, the bispecific antibody is used for treating tumor tissues with high expression or abnormal expression of the EGFR and other diseases caused by over-expression of the EGFR.

Herein, the complete monoclonal antibody is a full length antibody.

With the adoption of the above technical solutions, the invention includes beneficial technical effects as follows:

The bispecific antibody in the invention is in a form of tetravalent antibody, and this form of tetravalent antibody completely retains the antibody sequence binding to the tumor antigen and has a high affinity. Meanwhile, the tetravalent bispecific antibody can better connect the tumor cells and effector cells, thereby more conductive to the biological functions of the bispecific antibody. Compared with the common BITE bispecific antibody form, the molecule in the invention further includes Fc fragment; and the existing Fc fragment may prolong the half life of drug molecule in vivo, which enables the drug molecule to achieve better effects, lowers administration frequencies of patients and alleviates pain of the patients. The invention is used for treating the tumor tissues with high expression or abnormal expression of the EGFR and other diseases caused by over-expression of the EGFR.

BRIEF DESCRIPTION OF THE DRAWINGS

FIG. 1 schematically shows a molecular schematic diagram of a bispecific antibody;

FIG. 4 schematically shows detection of binding capacity of the bispecific molecule to an antigen by ELISA;

FIG. 5 schematically shows binding of the bispecific antibody and A431 cell;

DETAILED DESCRIPTION OF THE EMBODIMENTS

Figure 2:
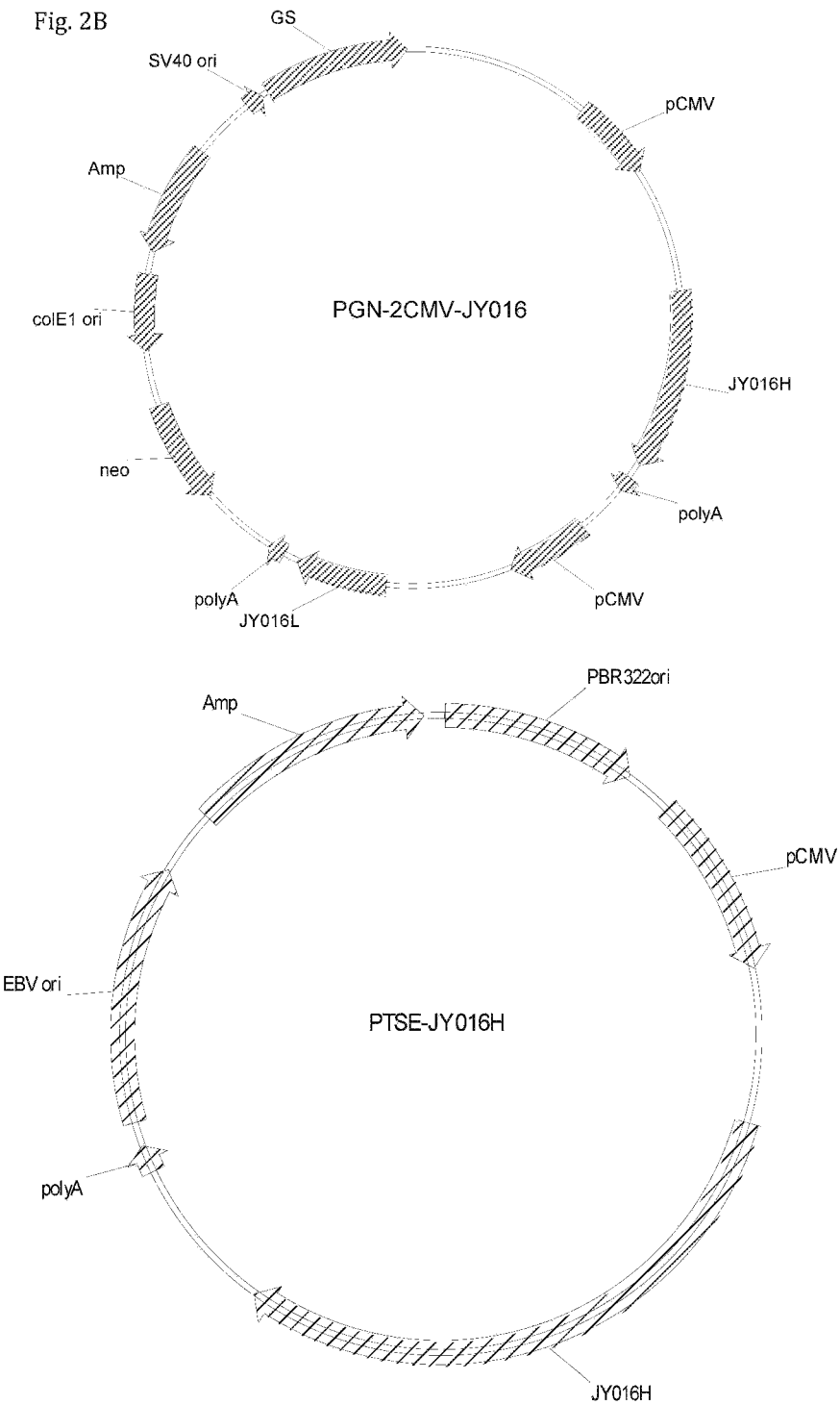
FIG. 2 schematically shows a construction diagram of bispecific molecule expression plasmid.

The invention is further described below in detail with the specific embodiments and in combination with drawings.

The invention provides an anti-EGFR and anti-CD3 bispecific antibody and the use thereof. The bispecific antibody includes (a) a complete monoclonal antibody, (b) a single-chain antibody ScFv and (c) a linker, herein the (a) specifically binds to an EGFR antigen and consists of two antibody heavy chains and two antibody light chains; the (b) specifically binds to an immune cell antigen CD3, and the (b) refers to two single-chain antibodies ScFv; the two single-chain antibodies ScFv of the (b) are respectively linked with C terminals of the two antibody heavy chains of the (a) by the (c) linker.

Further preferably, the (c) linker in the bispecific antibody has an amino acid sequence of $(GGGGX)_n$, X includes Ser or Ala, preferably Ser; and n is a natural number of 1-4, preferably 3.

Further preferably, the (a) complete monoclonal antibody in the bispecific antibody consists of two light chains and two heavy chains, each heavy chain and each light chain are connected by disulfide bonds, and the two heavy chains are connected by disulfide bonds in the hinge region. Variable regions of the heavy chains and the light chains specifically bind to EGFR antigen of tumor cell surface.

Further preferably, a heavy chain constant region of the (a) complete monoclonal antibody is one of IgG1, IgG2, IgG3 or IgG4, preferably IgG2.

Further preferably, an amino acid sequence of a heavy chain variable region of the (a) complete monoclonal antibody is one of SEQ ID NO 1, SEQ ID NO 2 or SEQ ID NO 3:

herein, SEQ ID NO 1 (an amino acid sequence of a heavy chain variable region of nimotuzumab):

QVQLQQPGAELVKPGASVKLSCKASGYTFTNYYIYMKQRPGQGLEWIGGI

NPTSGGSNFNEKFKTKATLTVDESSTTAYMQLSSLTSEDSAVYYCTRQGL

WFDSDGRGFDFWGQGTTLTVSS.

SEQ ID NO 2 (an amino acid sequence of a heavy chain variable region of cetuximab):

QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

SEQ ID NO 3 (an amino acid sequence of a heavy chain variable region of paniturnumab):

QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD

RVTGAFDIWGQGTMVTVSS.

Herein, an amino acid sequence of a light chain variable region of the (a) complete monoclonal antibody is one of SEQ ID NO 4, SEQ ID NO 5 or SEQ ID NO 6, SEQ ID NO 4 (an amino acid sequence of a light chain variable region of nimotuzumab):

DVLMTQIPLSLPVSLGDQASISCRSSQNIVHSNGNTYLDWYLQKPGQSPN

LLIYKVSNRFSGVPDRFRGSGSGTDFTLKISRVEAEDLGVYYCFQYSHVP

WTFGGGTKLEIK.

SEQ ID NO 5 (an amino acid sequence of a light chain variable region of cetuximab):

DILLTQSPVILSVSPGERVSFSCRASQSIGTNIHWYQQRTNGSPRLLIKY

ASESISGIPSRESGSGSGTDFTLSINSVESEDIADYYCQQNNNWPTTFGA

GTKLELK.

SEQ ID NO 6 (an amino acid sequence of a light chain variable region of panitumumab):

DIQMTQSPSSLSASVGDRVTITCQASQDISNYLNWYQQKPGKAPKLLIYD

ASNLETGVPSRFSGSGSGTDFTFTISSLQPEDIATYFCQHFDHLPLAFGG

GTKVEIK.

Further preferably, an amino acid sequence of a heavy chain variable region of the (b) single-chain antibody ScFv is SEQ ID NO 8, and an amino acid sequence of a light chain variable region of the (b) single-chain antibody ScFv is SEQ ID NO 9, herein SEQ ID NO 8 (an amino acid sequence of a heavy chain variable region of an anti-CD3 single-chain antibody):

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS.

SEQ ID NO 9 (an amino acid sequence of a light chain variable region of the anti-CD3 single-chain antibody):

DIQLTQSPAIMSASPGEKVTMTCRASSSVSYMNWYQQKSGTSPKRWIYDT

SKVASGVPYRFSGSGSGTSYSLTISSMEAEDAATYYCQQWSSNPLTFGAG

TKLELK.

Further preferably, amino acid sequences of the two single-chain antibodies ScFv of the (b) are shown as SEQ ID NO 7, herein, SEQ ID NO 7 (an amino acid sequence of an anti-CD3 single-chain antibody):

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSGGGGSGGGGSGGGGSDIQLTQSPAIMSASPG

EKVTMTCRASSSVSYMNWYQQKSGTSPKRWIYDTSKVASGVPYRFSGSGS

GTSYSLTISSMEAEDAATYYCQQWSSNPLTFGAGTKLELK.

Further preferably, each of the single-chain antibodies ScFv of the (b) consists of a heavy chain variable region, a (c) linker and a light chain variable region, the heavy chain variable region and the light chain variable region specifically bind to CD3 antigen of immune cell surface; and the (c) linker has an amino acid sequence of (GGGGS)$_n$, herein n is a natural number of 1-4, preferably (GGGGS)$_3$.

Further preferably, the constructed vector is transfected into a host cell, and the host cell include prokaryotic cell, yeast or mammalian cell, such as CHO cells, NS0 cells or other mammalian cells, preferably the CHO cells.

Further preferably, the bispecific antibody is used for treating tumor tissues with high expression or abnormal expression of the EGFR and other diseases caused by over-expression of the EGFR.

Specific Embodiment 1: Construction of an Expression Vector of Bispecific Antibody Molecule a) Construction of a Bispecific Transient Expression Vector Designing corresponding gene sequences according to the form of the bispecific antibody in FIG. 1. Selecting PTSE as an expression vector to clone and express anti-EGFR light chain genes and anti-EGFR heavy chain-CD3 ScFv fusion genes. Adding SalI and BamHI restriction sites into the light chain genes and the fusion genes on both sides of coding region sequences respectively, and the two genes are synthesized by Taihe Biotechnology (Beijing) Co., Ltd. and respectively cloned into a PUC19 vector. Transforming two plasmids into TOP competence (Huitian Dongfang, item No. HT702-03), performing minipreparation with a CWBio minipreparation kit (item No. CW0500), performing restriction digestion with restriction enzymes SalI-HF and BamHI-HF, performing homologous recombination, respectively obtaining expression vectors (schematic diagrams are shown in FIG. 2A and FIG. 2B) containing the light chain and fusion genes, and respectively naming plasmids as PTSE-JY016L-Tet131Ab and PTSE-JY016H-TetBiAb.

b) Construction of a Bispecific Stable Transformation Expression Vector

Selecting PGN-2CMV serving as an expression vector to clone and express anti-EGFR light chain genes and anti-EGFR heavy chain-CD3 ScFv fusion genes, the vector includes selection markers Neomycin and GS, two CMV promoters and corresponding structural units; designing primers of the light chain and fusion gene, introducing a Kozak sequence, a signal peptide and corresponding restriction enzyme cutting sites, and synthesizing by Taihe Biotechnology (Beijing) Co., Ltd.; taking the plasmids PTSE-JY016L-TetBiAb and PTSE-JY016H-TetBiAb as a template, performing PCR amplification to obtain corresponding bands, and performing homologous recombination with the vector (plasmid profiles are shown in FIG. 2C).

Specific Embodiment 2: Expression and Purification of the Bispecific Antibody Molecule a) Expression of a Tetravalent Antibody Plasmid maxi-preparation is performed by utilizing an endotoxin-free maxi kit (CWBio, CW2104), and specific operation steps are executed according to the specification provided by the kit.

Culturing human embryonic kidney cells (HEK293ES suspension cells) in Freestyle 293 Expression Medium (Gibco, 12338-026), subculturing cells once every one or two days, maintaining initial density of the subcultured cells at $0.2$-$0.6 \times 10^6$/ml, and a cell culture volume to be 15-35% of a shake flask volume, and placing the cell culture flask in a shaker (shaker speed: 135 rpm, temperature: 37° C., $CD_2$: 5%); subculturing HEK293ES cells that are located in a logarithmic phase and a good growth state to a flask with cell density of $0.5 \times 10^6$/ml the day before transfection, culturing overnight in the shaker (135 rpm, 37° C. 5% of $CO_2$), and transfecting the next day.

Culturing prepared cell suspension of $1 \times 10^6$/ml in a shaker (135 rpm, 39° C., 5% of $CO_2$) for 2 h before transfection, sequentially adding PTSE-antiEGFR—H-TetBiAb (having a final concentration of 0.5 μg/ml), PTSE-antiEGFR-L (having a final concentration of 0.5 μg/trip and polyethyleneimine (Sigma) (having a final concentration of 2 μg/ml) during transfection, uniformly mixing, co-transfecting into the HEK293ES suspension cells, and culturing in the shaker (135 rpm, 39° C., 5% of $CO_2$) for 40 min; continuously culturing the transfected cells in the shaker (135 rpm, 37° C., 5% of $CO_2$), and expressing the anti-EGFR.CD3 tetravalent antibody; and After transfecting for 96 hours, and then centrifuging to obtain expression supernatant.

b) Purification of the Tetravalent Bispecific Antibody

Figure 3:
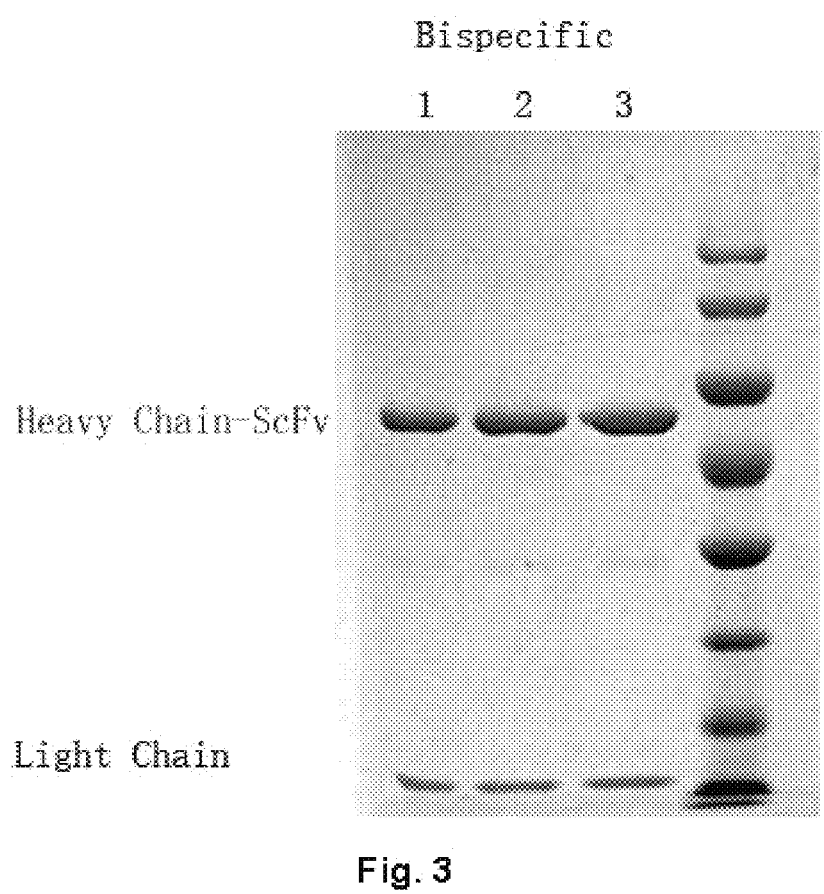
FIG. 3 schematically shows a denatured SDS electrophoretogram of the purified bispecific molecule.

Filtering the expression supernatant with a 0.22 μM filter membrane, and obtaining an antibody with the Fc domain from the expression supernatant utilizing an affinity chromatography column; respectively taking 50 mM Tris-HCl, 0.15M NaCl PH7.0 and 0.1M citric acid-sodium citrate PH3.0 as equilibration buffer and elution buffer; performing cation-exchange chromatography to obtain target bispecific antibody, herein the cation exchange column is HiTrap SP FF; equilibrating an SP chromatographic column with equilibration buffer 20 mM PB PH6.3, eluting with elution buffer 20 mMPB+1M NaCl (PH6.3), and finally solution changing concentration with PBS buffer. The purified bispecific molecular reduction SDS-PAGE, is shown as FIG. 3. Herein, the EGFR antibody sequence of Bispecific-1 is nimotuzumab sequence; the EGFR antibody sequence of Bispecific-2 is Cetuximab; and the EGFR antibody sequence of Bispecific-3 is Panitumumab.

Specific Embodiment 3: Bispecific Antibody Molecules Binding to CD3 and EGFR Molecules Enveloping the EGFR extracellular region or the dimmer of CD3E and CD3G subunit extracellular region with a carbonate buffer of PH9.6 overnight under the condition of 100 ng/well/100 μl at 4° C.; washing with 300 μl/well 0.1% of PBS (PBS-T) buffer for 5 times, and adding 1% of BSA-PBS to block at a room temperature for 2 h, adding different dilutions of bispecific antibodies or corresponding antibodies. The highest concentration of each bispecific antibody (or antibody) is 1 μM; diluting 3 times, forming 10 gradients, only adding PBS diluents into the last well to serve as a negative control, and incubating at 37° C. for 1 h; then washing with a 300 μl/well PBS-T solution for 5 times, and adding an Anti-Human Fc-HRP secondary antibody diluted at 1:40000 with 1% BSA-PBS, incubating at 37° C. for 1 h; and developing with a TMB developing kit, 100 μl/well, for 8 min at room temperature, then stopping developing with 2M $H_2SO_4$. 50 μl/well, and reading at 450 nm/630 nm. Experimental results are shown as FIG. 4. Capacities of all the bispecific antibodies binding to the EGFR are similar to capacities of corresponding monoclonal antibodies [the capacity of the bispecific antibody constructed from nimotuzumab binding to the EGFR is similar to that of nimotuzumab (FIG. 4A); the capacity of the bispecific antibody constructed from Cetuximab binding to the EGFR is similar to that of Cetuximab (FIG. 4B); and the capacity of the bispecific antibody constructed from Panitumumab binding to the EGFR, is similar to that of Panitumumab (FIG. 4C)]; while the capacities of the various bispecific antibodies binding to CD3E and CD3G dimmers are similar (FIG. 4D). Results show that the form of the bispecific antibody adopted in the invention almost completely retains original capacity of antibodies bound to antigens; and moreover, capacity of ScFv of CD3 bound to the CD3 is irrelevant to different antibodies connected thereby (FIG. 4D).

Figure 6:
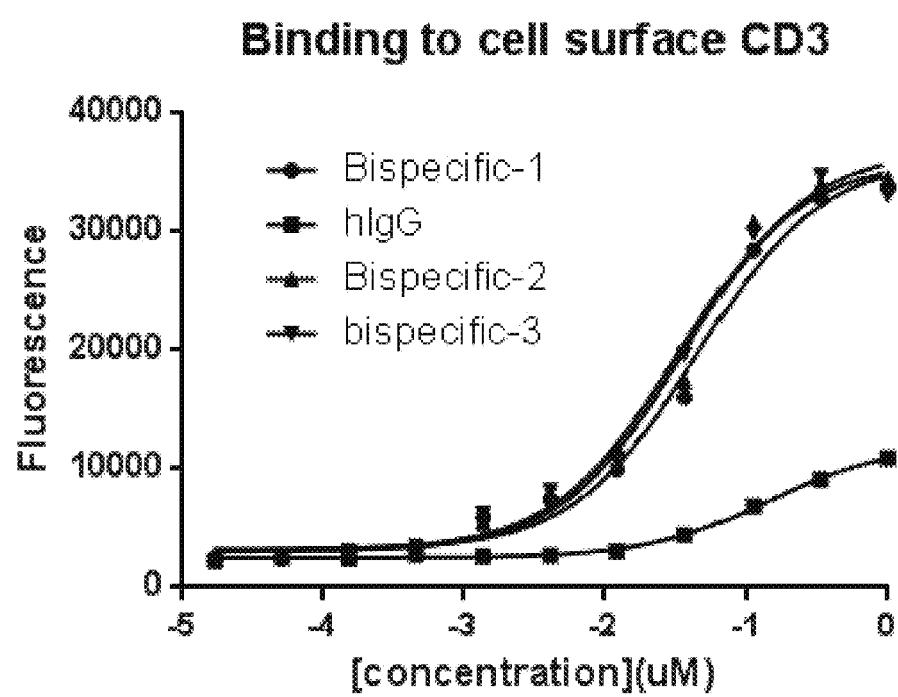
FIG. 6 schematically shows binding of the bispecific antibody and Jurkat cell.

Specific Embodiment 4: Bispecific Antibodies Molecules Binding to Over-Expressed EGFR or CD3 Cells a) Binding of Bispecific Antibodies and A431 Cells In the invention, the tumor cell line (A431) over-expressing EGFR is adopted for detecting binding of different bispecific antibodies and EGFR on cell surface, a corresponding antibody is used as a positive control, and human IgG (hIgG) is used as an isotype control. Digesting with 0.25% of trypsin, and centrifuging to collect the A431 cells; meanwhile diluting the various antibodies, controlling the highest concentration to 1 μM, and performing gradient dilution 3 times; washing the collected cells with PBS+1% BSA for three times, then adding the PBS+1% BSA to re-suspend the cells, spreading the cells in a 96-well plate at a dose of $1 \times 10^5$ cells per well, adding 100 μl of diluted bispecific antibodies, and incubating at a room temperature for 1 hour, centrifuging to remove the supernatant, washing the cells with PBS three times, then re-suspending the cells using a diluted Alexa488-labeled anti-human IgG-Fc antibody, incubating in darkness at the room temperature for 1 hour, washing with the PBS three times, re-suspending with 100 μl of PBS, and detecting fluorescence intensity by flow cytometry. Results are analyzed with Graphpad Prism. The results show that (FIG. 5), binding capacity of each bispecific antibody and A431 has comparability with that of a corresponding antibody thereof, while binding of hIgG and A431 is very weak. It is proved that, the bispecific antibody well maintains activity of parent antibody which specifically binds to EGFR on the cell surface b) Binding of Bispecific Antibodies and Jurkat Cells Jurkat cells over-express CD3 are used for detecting the binding of the bispecific antibodies and cell surface CD3. The experimental process of the binding of bispecific antibodies and Jurkat cells is similar to that of the embodiment 4a, and the difference is that the Jurkat cells are suspension cells, while the A431 cells are adherent cells. The Jurkat cells are collected by centrifugation, various antibodies are added, and the rest operations are the same as those in the A431 experiment. Results show that (FIG. 6), the capacity of binding isotype control to Jurkat is very weak; and different bispecific antibodies are capable of well binding to the cells, and capacities of the three bispecific antibodies binding to the Jurkat cells are consistent, which indicates that the capacity of the anti-CD3 ScFv in the bispecific antibody in FIG. 1 binding to the cell surface antigens is not influenced by any antibody connected thereby.

Specific Embodiment 5: The Killing Effect of the Bispecific Antibody Molecule Mediated PBMC on Effector Cells a) PKH26 Labeling in A431 or H520 Cells A431 is a tumor cell strain capable of over-expressing EGFR, while H520 does not express the EGFR. In the experiment, the A431 serves as an experimental cell strain, while the H520 serves as a negative control.

Adding $2\times10^6$ cells into a 1.5 ml centrifuge tube for centrifuging at 1500 rpm for 5 min, removing a complete medium, and respectively cleaning the cells twice with serum-free medium; re-suspending the cells with a Diluent C solution in a PKH26 kit, adding 2×PKH26 staining solution in equal volume (a proportion: dissolving 0.4 μl of stock staining solution into 1001 μl of Diluent C), uniformly mixing, and placing at a room temperature for 1 min; immediately adding the same volume of 0.5% BSA-PBS solution as that of the solution in the tube to terminate a reaction, adding 1 ml corresponding complete medium to dilute and re-suspend the cells, centrifuging at 1500 rpm for 5 min to collect a cell precipitate; and culturing the cells re-suspended by the complete medium in a cell culture bottle for later use.

b) PBMC Separation

Adding 20 ml mononuclear cell separating medium to a 50 ml tube, diluting a collected blood with a whole blood diluent according to a ratio of 1:1, after uniformly mixing, slowly spreading to an upper layer of the separating medium at a constant speed along inner walls of Corning tubes, and diluting in each tube until a whole blood volume is 20 ml; putting each tube filled with liquid into a centrifuge pre-cooled to 22° C. in advance, and horizontally centrifuging by 600 g for 15 min (setting acceleration and deceleration as 1); taking out the centrifuged tubes after centrifugation completion, carefully pipetting a cell layer-mononuclear cell (PBMC) in circular arc distribution between the separating medium and serum with a pipette, and placing in a new 50 ml tube; adding cell washing liquid into cell sap according to a ratio of 1:5, fully and uniformly mixing and centrifuging, removing the supernatant, repeatedly washing once, collecting the cell precipitate, re-suspending with an RPMI-1640 medium, and culturing the cells in a cell culture bottle for later use.

c) Magnetic Bead Separation of CD3+T Cells

PBS (Ph7.2, containing 0.5% BSA, 2 mM EDTA), filtering, sterilizing and avoiding bubbles.

Centrifuging to remove blood platelet (20° C., 200 g, 10-15 minutes), and removing cell aggregate with a 30 μm filter membrane; collecting PBMC cells by centrifugation at 200 g for 10 minutes, and removing the supernatant; re-suspending $2\times10^7$ cells in 60 μl buffer+20 μl FcR Blocking Reagent; adding 20 μl magnetic beads, uniformly mixing, and incubating at 2-8° C. for 15 minutes; adding 1-2 ml buffer, centrifuging at 300 g for 10 minutes, and removing the supernatant; re-suspending by 500 μl; placing a sorting column on a sorting rack, and rinsing by 500 μl; adding cell suspension, and collecting unbound cells; washing by 500 μl for three times after liquid on the top of the column drains running out; taking the sorting column down from the sorting rack, and placing in a collection tube, rapidly rinsing by 1 mil, collecting the cells, counting and observing a ratio of viable cells.

d) Detection of Bispecific Antibody Effect and Function

Diluting according to a ratio of 1:3 from a final concentration of 1 μM, and forming 10 gradients and 2 duplicate wells; setting 2 drug-free control wells, complementing the volume with a medium, then uniformly mixing marked A431 or H520 cells ($2\times10^4$ cells/well/50 μl) and CD3+T cells ($2\times10^5$ cells/well/50 μl) according to a needed usage amount, spreading the cells to each well of a V-bottom 96-well plate, and at the same time setting three flow control wells as follows: (1) unmarked Raji cells ($2\times10^4$ cells/well), (2) PKH26 marked cells ($2\times10^4$ cells/well), and (3) CD3+T cells ($2\times10^5$ cells/well); culturing for 18 hours, adding TO-PRO3 dye according to a ratio of 1:50000 after incubation completion, and incubating in darkness at 37° C. for 10 min; simultaneously setting a flow control (4) TO-PRO3 marked cells; and centrifuging at 3000 rpm for 5 min, removing partial medium supernatant, re-suspending with a 0.5% of BSA-PBS solution, and performing flow cytometer detection.

A calculation formula:

cell mortality rate %=(1-PKH26$^+$ TOPRO3$^-$ the number of cells (drug action group)/PKH26$^+$ TOPRO3$^-$ the number of cells (drug-free action group))×100 e) Result Analysis

Figure 7:
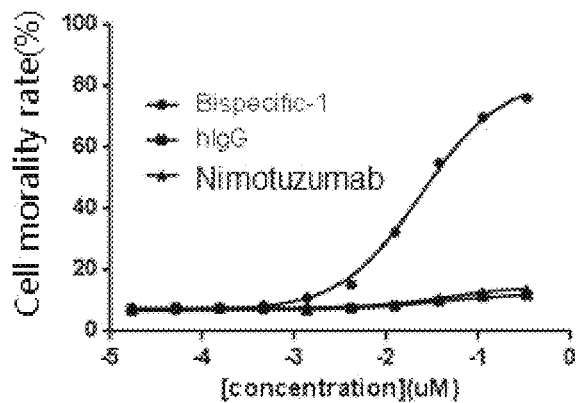
FIG. 7 schematically shows binding of the bispecific antibody-mediated PBMC to A431.
Figure 7:
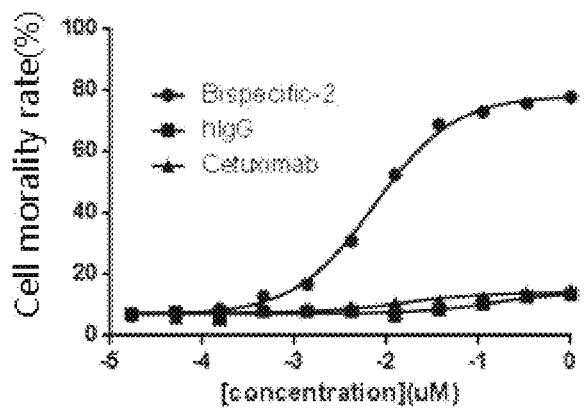
Figure 7:
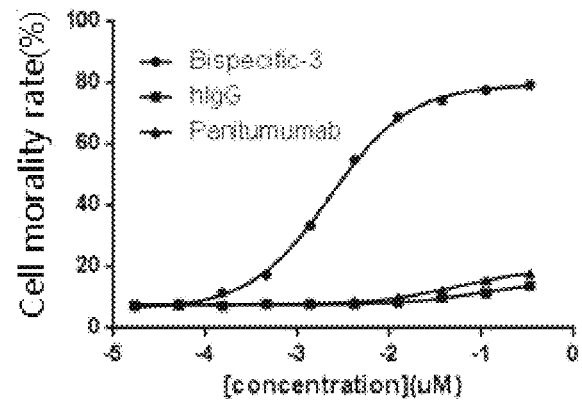
Figure 8:
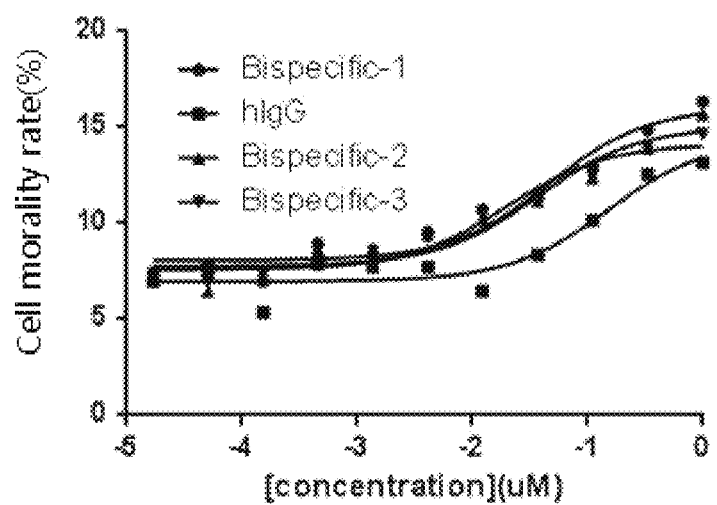
FIG. 8 schematically shows a killing effect of the bispecific antibody-mediated PBMC to H520.

As shown in FIG. 7, PBMC mediated by the bispecific antibody molecule has an excellent killing effect on A431 effector cells over-expressing the EGFR; while corresponding antibody and hIgG thereof have weak killing effect. Meanwhile, all the bispecific antibodies have very weak killing effect on H520 cells that do not express the EGFR, and have similar effect to isotype control hIgG (FIG. 8). This indicates that the killing effects of all the constructed bispecific antibodies on target cells are specific; and capacities of killing specific target cells of the three different bispecific antibodies are similar, and the cell mortality rate is about 80%. The above description shows that the bispecific antibodies in FIG. 1 have good biological activity.

The above are only preferred embodiments of the invention, and are not intended to limit the invention. For those skilled in the art, the invention is susceptible to various modifications and changes. Any modifications, equivalent replacements, improvements and the like made within the spirit and principle of the invention shall fall within the scope of the protection of the invention.

What is claimed is:

1. A bispecific antibody, comprising: (a) a complete monoclonal antibody, (b) two single-chain antibodies ScFv and (c) a linker, wherein the (a) specifically binds to an EGFR antigen and consists of two antibody heavy chains and two antibody light chains; the (b) specifically binds to an immune cell antigen Cluster-of-Differentiation 3 (CD3), and the two single-chain antibodies ScFv of the (b) are respectively linked with C terminals of the two antibody heavy chains of the (a) by the (c) linker;

wherein the amino acid sequence of a heavy chain variable region of the complete monoclonal antibody is SEQ ID NO 3 and the amino acid sequence of a light chain variable region of the complete monoclonal antibody is SEQ ID NO 6, wherein amino acid sequences of the two single-chain antibodies ScFv of the (b) are both SEQ ID NO 7; or an amino acid sequence of the heavy chain variable region of the (b) single-chain antibody ScFv is SEQ ID NO 8, and an amino acid sequence of the light chain variable region of the (b) single-chain antibody ScFv is SEQ ID NO 9.

2. The bispecific antibody as claimed in claim 1, wherein the (c) linker has an amino acid sequence of $(GGGGX)_n$, X is Ala or Ser; and n is a natural number of 1-4.

3. A pharmaceutical composition, wherein the pharmaceutical composition comprises: the bispecific antibody as claimed in claim 1, wherein the amino acid sequence of a heavy chain variable region of the complete monoclonal antibody is SEQ ID NO 3 and the amino acid sequence of a light chain variable region of the complete monoclonal antibody is SEQ ID NO 6, wherein amino acid sequences of the two single-chain antibodies ScFv of the (b) are both SEQ ID NO 7, or wherein an amino acid sequence of the heavy chain variable region of the (b) single-chain antibody ScFv is SEQ ID NO 8, and an amino acid sequence of the light chain variable region of the (b) single-chain antibody ScFv is SEQ ID NO 9.

4. A method for treating a tumor diseases caused by specifically expression of EGFR antigens, comprising:

administering the bispecific antibody as claimed in claim 1 to a subject in need thereof, wherein amino acid sequences of a heavy chain variable region and a light chain variable region of the (a) complete monoclonal antibody are SEQ ID NO 3 and SEQ ID NO 6, wherein amino acid sequences of the two single-chain antibodies ScFv of the (b) are both SEQ ID NO 7, or wherein an amino acid sequence of the heavy chain variable region of the (b) single-chain antibody ScFv is SEQ ID NO 8, and an amino acid sequence of the light chain variable region of the (b) single-chain antibody ScFv is SEQ ID NO 9.

5. The method as claimed in claim 4, wherein the (c) linker has an amino acid sequence of $(GGGGX)_n$, X is Ala or Ser; and n is a natural number of 1-4.

6. The pharmaceutical composition as claimed in claim 3, wherein the (c) linker has an amino acid sequence of $(GGGGX)_n$, X is Ala or Ser; and n is a natural number of 1-4.

7. The bispecific antibody as claimed in claim 2, wherein the X is Ser, and the n is 3.

8. The pharmaceutical composition as claimed in claim 6, wherein the X is Ser, and the n is 3.

9. The method as claimed in claim 5, wherein the X is Ser, and the n is 3.

* * * * *